United States Patent
Drewry et al.

[19]

[11] Patent Number: 6,149,651
[45] Date of Patent: *Nov. 21, 2000

[54] DEVICE FOR SUPPORTING WEAK BONY STRUCTURES

[75] Inventors: Troy Drewry; Michael C. Sherman, both of Memphis, Tenn.

[73] Assignee: SDGI Holdings, Inc., Memphis, Tenn.

[*] Notice: This patent is subject to a terminal disclaimer.

[21] Appl. No.: 09/266,326

[22] Filed: Mar. 11, 1999

Related U.S. Application Data

[63] Continuation of application No. 08/867,628, Jun. 2, 1997, Pat. No. 5,897,556.

[51] Int. Cl.$^7$ .................................................. A61B 17/56
[52] U.S. Cl. ........................ 606/61; 623/17.11; 623/17.16
[58] Field of Search .................... 606/54, 60, 61, 606/62, 69, 70, 76, 77; 623/16, 17, 17.11, 17.16

[56] References Cited

U.S. PATENT DOCUMENTS

| | | | |
|---|---|---|---|
| 4,328,593 | 5/1982 | Sutter et al. ................................ | 3/1.91 |
| 4,501,269 | 2/1985 | Bagby . | |
| 4,820,305 | 4/1989 | Harms et al. .............................. | 623/16 |
| 5,015,247 | 5/1991 | Michelson ................................. | 606/61 |
| 5,211,664 | 5/1993 | Tepic et al. ................................ | 623/16 |
| 5,405,391 | 4/1995 | Hednerson et al. ....................... | 623/17 |
| 5,425,772 | 6/1995 | Brantigan ................................... | 623/17 |
| 5,489,308 | 2/1996 | Kuslich et al. ............................ | 623/17 |
| 5,496,372 | 3/1996 | Hamamoto et al. ...................... | 623/16 |
| 5,571,192 | 11/1996 | Schonhoffer .............................. | 623/17 |
| 5,593,409 | 1/1997 | Michelson ................................. | 606/61 |
| 5,609,637 | 3/1997 | Bidermann et al. ...................... | 623/17 |
| 5,645,598 | 7/1997 | Brosnahan, III .......................... | 623/17 |
| 5,658,337 | 8/1997 | Kohrs et al. ............................... | 623/17 |
| 5,669,909 | 9/1997 | Zdeblick et al. .......................... | 606/61 |

OTHER PUBLICATIONS

*TiMesh*, Sofamor Danek, 1996, author unknown.

*Primary Examiner*—Michael Buiz
*Assistant Examiner*—David O. Reip
*Attorney, Agent, or Firm*—Woodard, Emhardt, Naughton, Moriarty & McNett

[57] ABSTRACT

A device for supporting weak bony structures comprises an elongated tubular body having first and second ends configured for contacting adjacent bony structures. A tubular body is formed by a plurality of intersecting elongate bars with a first group of bars having their longitudinal axes arranged perpendicular to the axis of the tubular body, and a second group of bars having their axes arranged at non-perpendicular angles relative to the body axis. The tubular body also includes a plurality of joints formed by the intersection of two perpendicular bars and four angled bars. The ends of the tubular body are defined only by the intersection of angled bars. The ends include a plurality of substantially flat end surfaces that have a surface area greater than the combined cross-sectional areas of the intersecting angled bars forming the joints at the end of the body. In a preferred embodiment, the end surfaces have an undercut between the surfaces and the intersecting angled bars. The tubular body can assume various shapes when viewed from an end, such as circular and non-circular shapes including at least one flat side.

30 Claims, 2 Drawing Sheets

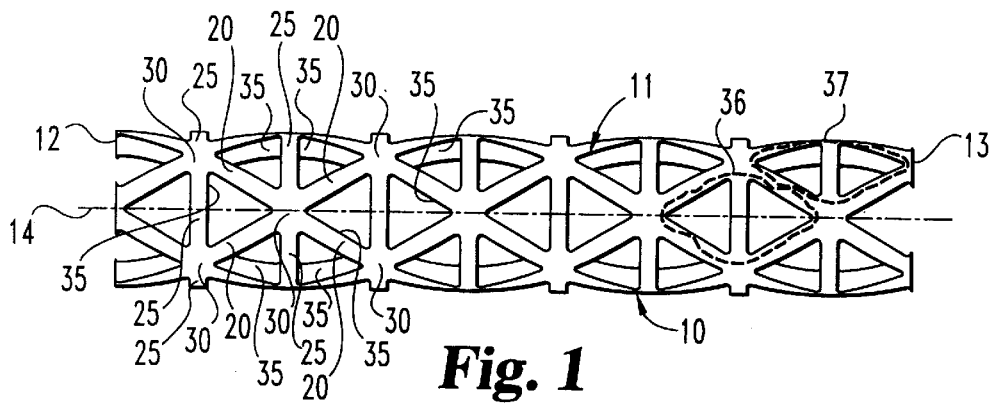
Fig. 1
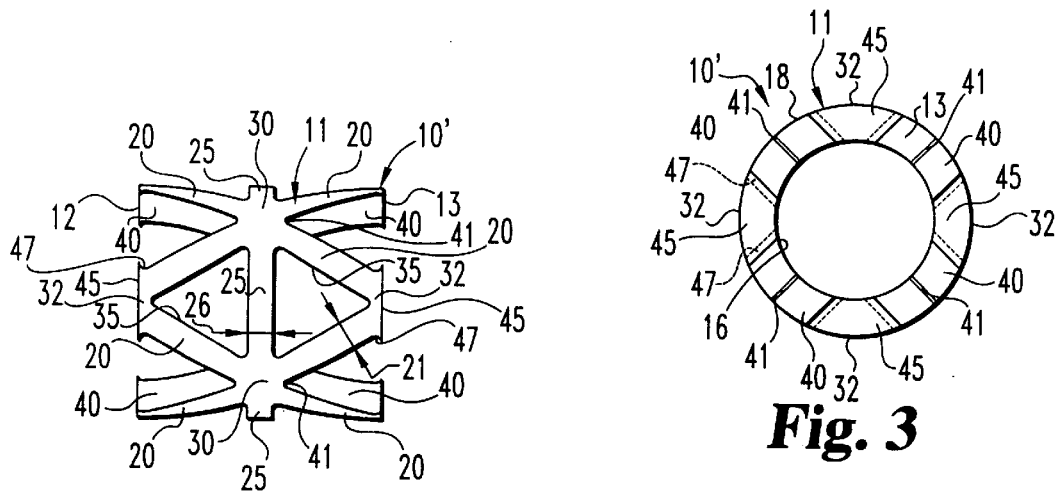
Fig. 2
Fig. 3
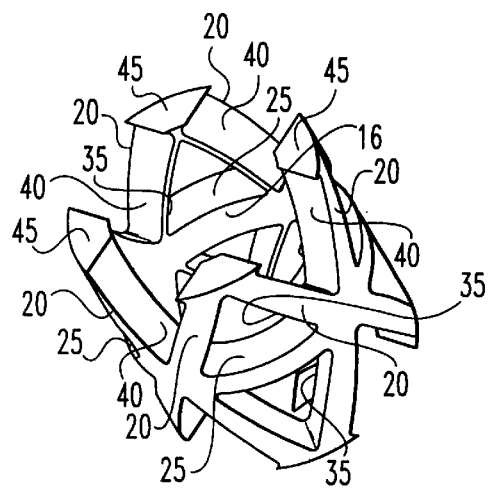
Fig. 4

DEVICE FOR SUPPORTING WEAK BONY STRUCTURES

This application is a continuation of U.S. application Ser. No. 08/867,628, filed on Jun. 2, 1997, now U.S. Pat. No. 5,897,556.

BACKGROUND OF THE INVENTION

The present invention concerns a device for supporting weak, bony structures, In particular, the device is in the form of an elongated cage for contacting adjacent bony structures in which the cage can be filled with osteogenetic or bone growth inducing material.

The repair and reconstruction of bony structures is sometimes accomplished by directly fixing adjacent bony structures to each other, such as by a plate. In other instances, bone growth inducing material can be introduced between the adjacent bony structures, which over time results in a solid bony connection. In some instances, the adjacent bony structures are not sufficiently strong to maintain their patency as the bone heals or the bone grows between the adjacent structures through the bone growth inducing material. In these instances, mesh structures or cages have been provided to engage the adjacent bony structures to provide additional stability. The cages are generally hollow and can be configured to contact the harder cortical bone of the adjacent bony structures. The hollow portion of the cages can be filled with bone growth inducing material.

SUMMARY OF THE INVENTION

A device for supporting weak bony structures comprises an elongated tubular body having a first end and a second end for contacting adjacent bony structures and a body axis along its length between the ends. The tubular body is formed by a plurality of intersecting elongate bars, a first group of the bars having longitudinal axes arranged perpendicular to the body axis and a second group of said bars having longitudinal axes arranged at non-perpendicular angles relative to the body axis. A plurality of joints are formed by the intersection of two perpendicular bars from the first group and four angled bars from the second group. The tubular body further comprises a plurality of triangular apertures defined by one bar from the first group and two bars from the second group.

In one aspect of the device, the tubular body includes at least one circumferential row of bars from the first group defining a plane perpendicular to the body axis. In some embodiments, the body includes multiple circumferential rows of bars from the first group, all defining substantially parallel planes that are perpendicular to the body axis.

A further aspect of the invention, the first end of the body is formed only by a plurality of end joints formed by intersecting pairs of angled bars from the second group. The end joints each define flat surfaces for contacting the bony structure, the flat surfaces defining a plane that is substantially perpendicular to the body axis. In one feature, each of the intersecting pairs of bars define a combined cross-sectional area perpendicular to the longitudinal axes of the bars. Each of the flat surfaces defines an end area contacting the bony structure that is greater than the combined cross-sectional area of the pair of intersecting angled bars. In one embodiment each of the flat surfaces is substantially triangular in shape, while in another version, each of the flat surfaces is substantially trapezoidal in shape. Preferably, the flat surfaces define an undercut between the surface and the intersecting angled bars at the end joint.

In another aspect, the device for supporting weak bony structures comprises an elongated tubular body having a first end and a second end for contacting a bony structure and defining a body axis along its length between the ends. The tubular body is formed by a cylindrical wall, the wall defining a plurality of sets of triangular openings aligned parallel with the body axis. Adjacent ones of the plurality of sets are axially offset relative to each other along the body axis. In the preferred embodiment, the sets of openings include pairs of oppositely directed triangular openings.

It is one object of the present invention to provide a device for supporting weak bony structures that includes a chamber for receiving osteogenetic material. A further object resides in features of the device that provide a strong structure that can readily engage adjacent bony structures.

Other object and particular advantages of the present invention can be discerned from the following written description and accompanying figures.

DESCRIPTION OF THE FIGURES

FIG. 1 is a side elevational view of a device for supporting weak bony structures in accordance with one embodiment of the present invention.

FIG. 2 is a side elevational view of a further embodiment of a device for supporting weak bony structures.

FIG. 3 is an end elevational view of the device shown in FIG. 2.

FIG. 4 is a top perspective view of the device shown in FIGS. 2 and 3.

DESCRIPTION OF THE PREFERRED EMBODIMENTS

Figure 5:
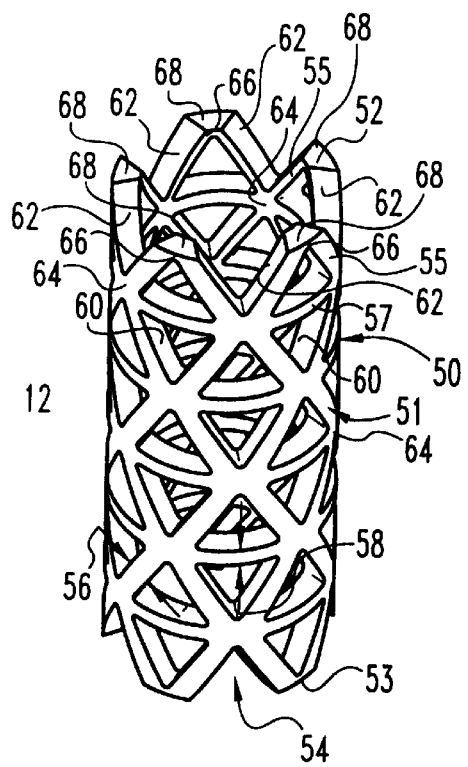
FIG. 5 is a side perspective view of a further embodiment of the device for supporting weak bony structures according to the present invention.

For the purpose of promoting an understanding of the principles of the invention reference will now be made to preferred embodiments thereof and specific language will be used to describe the same. It will nevertheless be understood that no limitation of the scope of the invention is thereby intended, such alterations and further modifications in the invention, and such further applications of the principles of the invention as described therein being contemplated as would normally occur to one skilled in the art to which the invention relates.

The present invention contemplates a device for supporting weak bony structures. In some aspects of the present invention, the device is intended to replace current mesh or cage-type devices for engagement with adjacent bony structures. In the preferred embodiment, the present inventive device includes a tubular body defining a hollow chamber. The adjacent bony structures can be at least partially received within the hollow chamber, and/or the chamber can be filled with bone growth inducing or osteogenetic material. In a further feature of the invention, the ends of the device are provided with flattened end surfaces at the junction between bars defining the tubular body. The end surfaces can be configured to engage the cortical bone of the adjacent bony structures.

In one embodiment of the invention shown in FIGS. 1–4, a device 10, 10' includes an elongated tubular body 11 formed along a longitudinal axis 14 having a first end 12 and a opposite second end 13. The devices 10, 10' defines a hollow chamber 16, as shown in FIGS. 3 and 4. The devices also define, in the illustrated embodiments, a substantially cylindrical outer surface 18.

In accordance with the invention, the tubular body 11 is formed by a first group of bars 20 and a second group of bars 25. The first group of bars are oriented at non-perpendicular or non-parallel angles relative to the longitudinal axis 14 of the body 11. For clarity, the members of this first group of bars will be identified as angled bars 20. The second group of bars are aligned with their axes substantially perpendicular to the longitudinal axis 14 of the tubular body. The outer surfaces of the bars 20, 25 define the cylindrical outer surface 18.

Further in accordance with the invention, the groups of bars are connected to each other at a plurality of interior joints 30. In accordance with one aspect of the invention, two perpendicular bars 25 and four angled bars 20 converge at a single joint 30. It has been found that this arrangement of angled bars 20 and perpendicular bars 25, as well as the configuration of the interior joints 30, provides the device 10 with substantial axial, torsional and bending strength.

In a further aspect of the invention, the tubular body includes end joints 32 which are formed by the intersection or union of a pair of angled bars 20. As can be seen from FIG. 1, the first end 12 and second end 13 of the tubular body 11 do not terminate with a number of perpendicular bars 25, but instead terminate only with the end joints 32 formed by the intersection of angled bars 20.

With the illustrated arrangement of angled bars 20 and perpendicular bars 25, the tubular body 11 defines a plurality of triangular openings 35. Each triangular opening is defined by two angled bars 20 and one perpendicular bar 25. In accordance with the preferred embodiment, the plurality of triangular openings 35 can be divided into two sets of openings 36, 37. In the first set 36, pairs of oppositely directed triangular openings 35 are spaced axially along the length of the tubular body 11. In the second set 37, similar pairs of oppositely directed triangular openings are axially offset from the pairs of openings in the first set 36, relative to the longitudinal axis 14 of the body 11. Put in other terms, the triangular openings are defined by the bars 20, 25 in pairs of oppositely facing triangles, with successive pairs of openings being staggered circumferentially around the body 11 and along the length of the body. The oppositely directed triangles share a common perpendicular bar defining the base of the triangle. As with the definition of the interior joints 30, it has been found that the pattern of triangular openings 35 enhances the overall stiffness and strength of the devices 10, 10'.

In a further aspect of the invention, the body 11 further defines end triangular openings 40 that are open at the opposite ends 12 and 13. In particular, the end triangular openings 40 are defined by a pair of angled bars 20 emanating from a vertex 41 at an interior joint 30, as shown in FIG. 2.

The present invention provides another novel feature at the end joints 32. In particular, an end surface 45 is defined at the end joints 32 that is substantially flat. In accordance with the present invention, the end surface 45 defines a surface area that is greater than the cross-sectional area of the angled bars 20 joined at the end joints 32. For example, in one embodiment, the angled bars 20 have a width 21, while the perpendicular bars 25 have a smaller width 26. The angled bars have a cross-sectional area that is the square of the width 26 of the bars 20. The end surface, then, has a surface area that is greater than the combined cross-sectional area of two angled bars 20, or in other words greater than four times the width 21. In one functional aspect of the invention, this enlarged end surface 45 at each of the end joints 32 provides a broader area of contact between the first and second ends 12, 13 of the devices 10, 10' and the adjacent bony structures. In some embodiments, the devices 10, 10' may be disposed co-linearly between adjacent bony structures so that the ends would be in direct contact with the cortical ring of the bony structures. In this instance, the greater surface area of the flat end surfaces 45 will dissipate the load pressure passing from each of the end joints 32 to the adjacent bony structures.

In yet a further aspect of the invention, the end joints 32 define an undercut 47 beneath the end surface 45, as shown in FIG. 2. This undercut 47 is preferably in the form of a radius from the end surface to the angled bars 20 intersecting at the end joints 32. In one aspect of this feature, the undercuts 47 of each of the end joints 32 can provide an edge for engaging the outer surface of adjacent bony structures to prevent migration of the devices 10, 10' relative to the bony structures.

The embodiment of the device 10 shown in FIG. 1 includes eight rows of perpendicular bars 25 and eight rows of pairs of triangular openings. In this embodiment, the tubular body 11 can have an outer diameter of about 10 mm, an inner diameter of the hollow chamber 16 of about 6.5 mm, and an overall length of about 50 mm. Of course, the diameters and length can be adjusted depending upon the dimensions of the triangular openings. In this specific embodiment, the triangular openings have a height of about 4 mm, and form an equilateral triangle. In this specific embodiment as well, the pairs of triangular openings are situated at 45 degree intervals around the circumference of the tubular body 11. Furthermore, the angled bars 20 are arranged to subtend approximately a 60 degree angle. Again in this specific embodiment, the width 21 of the angled bars 20 is about 1.14 mm, while the width 25 of the perpendicular bars 25 is slightly less at about 1.0 mm.

In a second embodiment, the device 10', as shown in FIGS. 2–4, includes only one row of perpendicular bars 25 and one row of pairs of triangular openings 35. In this embodiment, the device 10' can have an overall length of about 10 mm with similar outer and inner diameters to the device 10 of FIG. 1.

In the embodiments shown in FIGS. 1–4, the devices 10, 10' include four discreet end surfaces 45, each separated by 90 degrees. In the embodiment of FIG. 1, the device 10 includes eight rows of triangular openings evenly distributed around the circumference of the tubular body 11. In the embodiment of FIG. 2, the device 10' includes only four such triangular openings 35 with four end triangular openings being interspersed at the first and second ends 12, 13 of the body 11.

In an alternative embodiment, a device 50 shown in FIG. 5 includes a tubular body 51 having a first end 52 and a second end 53. The body 11 is defined by a plurality of angled bar 55 and perpendicular bars 57 that are substantially similar to the like-named components of the devices 10, 10'. Similarly, the tubular body 51 defines a plurality of interior triangular openings 60 and triangular end opening 62, as well as an interior joints 64 and end joints 66.

The device 50 further includes end surfaces 68 that are similar in configuration to the end surfaces 45 of the previous embodiments. However, unlike the devices 10, 10', the device 50 of FIG. 5 includes five such end surfaces 68 evenly circumferentially distributed around the first end 52 and second end 53. Correspondingly, the device 50 includes 10 rows of interior triangular openings 60 and five end triangular openings 62 at each end 52, 53 of the device 50. The triangular openings 60 still retain the equilateral triangle configuration found in the devices 10, 10'.

In a specific embodiment of the device 50, the angled bars 55 have a width 56 of about 1.3 mm, which is less than the width of the angled bars 20 of the previous embodiment. The perpendicular bars 57 have a width 58 that is about 1 mm, which is the same as the width of the perpendicular bars 25 of the devices 10, 10'. Because additional end surfaces 68 are provided, the device 50 preferably has an outer diameter that is greater than the outer diameter of the devices 10, 10' that have only four such end surfaces. In a specific embodiment, the device 50 can have an outer diameter of about 13 mm and an inner diameter for the hollow chamber 54 of about 10 mm. As with the devices 10, 10', the end surfaces 68 have surface areas that are greater and the combined cross-sectional area of the angled bars 55 intersecting at the end joints 66. Also, like the prior embodiment, the end surfaces 68 preferably have an undercut, similar to the undercut 47 shown in FIG. 2.

Figure 6:
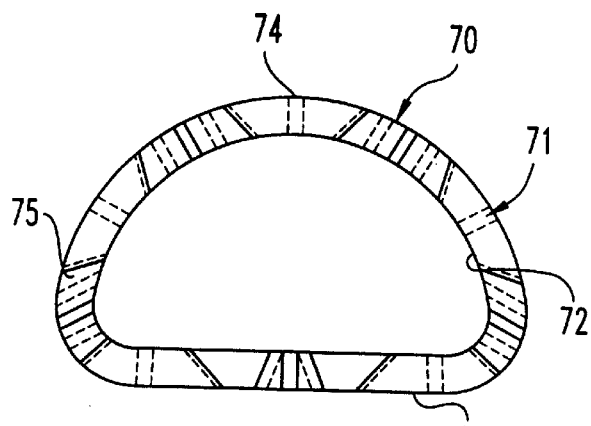
FIG. 6 is a top elevational view of yet another embodiment of the present invention showing a non-circular profile.

The embodiments of the device for supporting weak bony structures as shown in FIGS. 1–5 are cylindrical in configuration, having circular cross-sections that are substantially constant throughout the length of the devices. In another embodiment, the external configuration of the device can be modified according to the bony structures for which the device is intended. For example, in FIG. 6, a device 70 is shown formed by a tubular body 71 defining a hollow chamber 72. Unlike the previous cylindrical or circular embodiments, the device 70 has a non-circular cross-section or end view. In this embodiment of the invention, the device 70 includes outer surface 73 and a partially elliptical or ovate outer surface 74. In the illustrated embodiment, the device 70 includes five end surfaces uniformly distributed around the perimeter of the tubular body 71. It is understood, however, that more or fewer such end surfaces could be provided.

Figure 7:
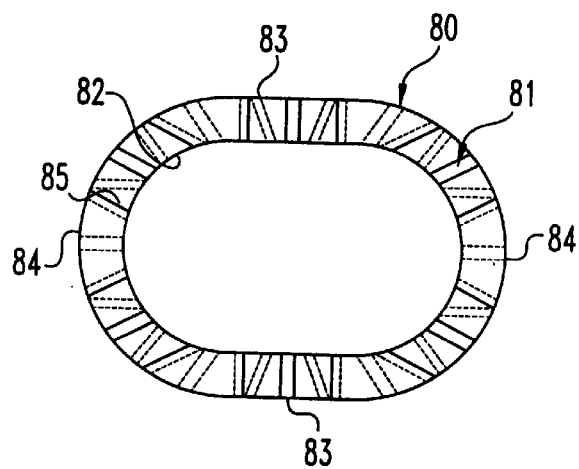
FIG. 7 is an end elevational view of another embodiment of the invention showing a non-circular profile.

In a further alternative embodiment, a device 80 shown in FIG. 7 includes a tubular body 81 defining a hollow chamber 82. Again, the device 80 has a non-circular cross-section or configuration along its length. In this embodiment, the tubular body 81 includes opposite flat outer surfaces 83 and opposite curved outer surfaces 84. In the specific embodiment, the curved outer surfaces are partially circular. In the specific embodiment of device 80, the tubular body 81 includes six end surfaces 85 uniformly distributed around the circumference or perimeter of the body. As with the previous embodiments, more or fewer such end surfaces can be provided. Likewise, the device 80, as well as the device 70, can be provided in various lengths, depending upon the adjacent bony structure.

Each of the devices 10, 10', 50, 70 and 80 shown in the Figures is preferably formed of a biocompatible material. The material is also preferably strong enough to withstand the application of external compressive, axial, torsional and bending loads, as well as being strong enough to provide support for the adjacent weak bony structures. In a preferred embodiment, the devices are formed entirely of titanium. Other biocompatible metals can be used such as surgical grade stainless steel. While the devices of the preferred embodiments are formed of a solid metallic material, the present invention also contemplates forming the devices of a porous, yet strong, material. For example, the devices could be formed from a porous tantalum material, such as the material HEDROCEL® provided by Implex Corporation.

In use, each of the devices 10, 10', 50, 70 and 80 can be engaged around the ends of adjacent bony structures. The devices can be used to hold the adjacent bony structures in immediate contact. Alternatively, the devices can hold the bony structures apart so that a gap is formed between the structures. In this instance, the hollow chambers of each of the devices can be filled with bone growth inducing or osteogenetic material. In these embodiments, any suitable osteogenetic material or composition is contemplated, including autograft, allograft, xenograft, demineralized bone, synthetic and natural bone graft substitutes, such as bioceramics and polymers, and osteoinductive factors. Where bony material is placed within the chambers, the material can be re-packed into the hollow chamber of the device, or can even be pushed through the plurality of triangular openings 35 once the device is in position. In some cases, the bone growth inducing materials require a separate carrier to hold the materials within the gap between the adjacent bony structures. These carries can include collagen-based carriers, or even bioceramic materials, such as BIOGLASS®, hydroxyapetite and calcium phosphate compositions. Moreover, some of the osteogenetic compositions contained within the devices of the present invention can comprise a therapeutically effective amount of a bone morphogenetic protein held within a suitable carrier material. The carrier material can be provided in the form of a sponge, a block, or even a folded sheet.

In an alternative use of the devices of the present invention, the devices can be directly and entirely situated in the gap between adjacent bony structures. In this instance, the end surfaces, such as end surface 45 of device 10', will directly contact the bone. Most preferably, the end surfaces will only contact the hard cortical bone at the outer perimeter of the bony structure. When used in this manner, the devices are most preferably packed with an osteogenetic material as described above.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, the undercut 47 (FIG. 2) can be eliminated for certain uses of the devices 10, 10'. The undercut can be eliminated by cutting the end joint 32 closer to the ends of the two angled bars 20 to form the end surface 45. In a further modification, the devices 10, 10', 50, 70 and 80 can be cut to various lengths to accommodate variations in the anatomy of the bony structures.

What is claimed is:

1. A device for supporting weak bony structures, comprising an elongated tubular body having a first end and a second end for contacting a bony structure, and having a body tube axis along its length between said ends, said tubular body formed by a plurality of intersecting elongate bars, a first group of said bars having longitudinal axes arranged perpendicular to the body tube axis and forming continuous rings perpendicular to the body tube axis, and a second group of said bars having longitudinal axes arranged transverse to said body tube axis at non-perpendicular angles relative to said body tube axis.

2. The device for supporting weak bony structures of claim 1, wherein said tubular body includes a plurality of joints, at least some joints of said plurality being formed by the intersection of two bars from said first group with four bars from said second group.

3. The device for supporting weak bony structures of claim 1, wherein said tubular body includes at least one circumferential row of bars from said first group defining a plane perpendicular to said body axis.

4. The device for supporting weak bony structures of claim 3, wherein said tubular body includes at least two circumferential rows of bars from said first group, said rows defining substantially parallel planes that are perpendicular to said body axis.

5. The device for supporting weak bony structures of claim 1, wherein said first end and said second end of said body is formed by a plurality of end joints formed by only intersecting pairs of bars from said second group, exclusive of bars from said first group.

6. The device for supporting weak bony structures of claim 5, wherein said end joints each define flat surfaces for contacting the bony structure, said flat surfaces defining a plane that is substantially perpendicular to said body axis.

7. The device for supporting weak bony structures of claim 6, wherein:
each bar of said intersecting pairs of bars defines a cross-sectional area perpendicular to the longitudinal axes of said bar; and
each of said flat surfaces defines an end area contacting the bony structure that is greater than said cross-sectional area.

8. The device for supporting weak bony structures of claim 6, wherein each of said flat surfaces is substantially triangular in shape.

9. The device for supporting weak bony structure of claim 6, wherein each of said flat surfaces is substantially trapezoidal in shape.

10. The device for supporting weak bony structures of claim 6, wherein each of said end joints define an undercut between said flat surfaces and said intersecting pair of bars forming said end joints.

11. The device for supporting weak bony structures of claim 1, wherein said body defines a hollow chamber for receiving bone growth inducing material.

12. A device for supporting weak bony structures, comprising an elongated tubular body, said tubular body having a length and a body tube axis extending along said length, said tubular body including:
a plurality of intersecting elongate bars, a first group of said bars including at least one circumferential row of bars defining a plane perpendicular to the body tube axis, and a second group of said bars having longitudinal axes arranged at non-perpendicular angles relative to said body tube axis; and
a first end and a second end along said axis for contacting a bony structure, said first and second ends each including a plurality of end joints having a contact surface formed by the intersection of said second group of bars, exclusive of bars from said first group.

13. The device for supporting weak bony structures of claim 12, wherein said at least one circumferential row of bars forms a ring around said axis.

14. The device for supporting weak bony structures of claim 12, wherein said end joints define flat surfaces for contacting the bony structure, said flat surface defining a plane that is substantially perpendicular to said body axis.

15. The device for supporting weak bony structures of claim 14, wherein:
each bar of said plurality of intersecting elongate bars defines a cross-sectional area of the bar perpendicular to the longitudinal axes of said bar; and
each of said flat surfaces defines an end area that is greater than said cross-sectional area for contacting the bony structure.

16. The device for supporting weak bony structures of claim 15, wherein each of said flat surfaces is substantially triangular in shape.

17. The device for supporting weak bony structures of claim 15, wherein each of said flat surfaces is substantially trapezoidal in shape.

18. The device for supporting weak bony structures of claim 15, wherein each of said joints defines an undercut between said flat surfaces and said plurality of intersecting elongate bars forming said end joints.

19. A device for supporting weak bony structures, comprising an elongated tubular body having a first end and a second end for contacting a bony structure, and having a body tube axis along its length between said ends, said tubular body formed by a plurality of intersecting elongate bars, a first group of said bars having longitudinal axes arranged perpendicular to the body tube axis and forming at least one continuous ring perpendicular to the body tube axis, and a second group of said bars having longitudinal axes arranged at non-perpendicular angles relative to said body tube axis, wherein said tubular body includes a plurality of joints, at least some joints of said plurality being formed by the intersection of two bars from said first group with four bars from said second group.

20. The device for supporting weak bony structures of claim 19, wherein said tubular body includes at least two circumferential rows of bars from said first group, said rows defining substantially parallel planes that are perpendicular to said body axis.

21. The device for supporting weak bony structures of claim 19, wherein said first end and said second end of said body is formed by a plurality of end joints formed by only intersecting pairs of bars from said second group, exclusive of bars from said first group.

22. The device for supporting weak bony structures of claim 19, wherein said at least one circumferential row of bars forms a ring around said axis.

23. A device for supporting weak bony structures, comprising an elongated tubular body having a first end and a second end for contacting a bony structure, and having a body tube axis along its length between said ends, said tubular body formed by a plurality of intersecting elongate bars, a first group of said bars having longitudinal axes arranged perpendicular to the body tube axis and forming continuous rings perpendicular to the body tube axis, and a second group of said bars having longitudinal axes arranged at non-perpendicular angles relative to said body tube axis, wherein said first end and said second end of said body is formed by a plurality of end joints formed by only intersecting pairs of bars from said second group, exclusive of bars from said first group.

24. The device for supporting weak bony structures of claim 23, wherein said tubular body includes a plurality of joints, at least some joints of said plurality being formed by the intersection of two bars from said first group with four bars from said second group.

25. The device for supporting weak bony structures of claim 23, wherein said end joints each define flat surfaces for contacting the bony structure, said flat surfaces defining a plane that is substantially perpendicular to said body axis.

26. The device for supporting weak bony structures of claim 25, wherein:
each bar of said plurality of intersecting elongate bars defines a cross-sectional area perpendicular to the longitudinal axes of said bar; and each of said flat surfaces defines an end area contacting the bony structure that is greater than said cross-sectional area.

27. The device for supporting weak bony structures of claim 25, wherein each of said flat surfaces is substantially triangular in shape.

28. The device for supporting weak bony structure of claim 25, wherein each of said flat surfaces is substantially trapezoidal in shape.

29. The device for supporting weak bony structures of claim 25, wherein each of said end joints define an undercut between said flat surfaces and said plurality of intersecting elongate bars forming said end joints.

30. The device for supporting weak bony structures of claim 23, wherein said body defines a hollow chamber for receiving bone growth inducing material.

* * * * *